(12) United States Patent
Simek et al.

(10) Patent No.: US 8,319,494 B2
(45) Date of Patent: Nov. 27, 2012

(54) PIPELINE INSPECTION TOOL WITH DOUBLE SPIRAL EMAT SENSOR ARRAY

(75) Inventors: James Simek, Sandy, UT (US); Jed Ludlow, Bountiful, UT (US); John H. Flora, Lynchburg, VA (US); Syed M. Ali, Lynchburg, VA (US); Huidong Gao, Forest, VA (US)

(73) Assignee: TDW Delaware Inc., Wilmington, DE (US)

( * ) Notice: Subject to any disclaimer, the term of this patent is extended or adjusted under 35 U.S.C. 154(b) by 581 days.

(21) Appl. No.: 12/642,031

(22) Filed: Dec. 18, 2009

(65) Prior Publication Data

US 2010/0327858 A1  Dec. 30, 2010

Related U.S. Application Data

(60) Provisional application No. 61/230,879, filed on Aug. 3, 2009, provisional application No. 61/220,734, filed on Jun. 26, 2009.

(51) Int. Cl.
*G01R 19/18* (2006.01)
*G01R 19/22* (2006.01)

(52) U.S. Cl. ........ 324/220; 324/219; 324/228; 324/229; 324/232; 324/233; 324/234; 324/236; 324/237; 324/238; 324/239; 324/240; 324/241; 324/242; 324/243

(58) Field of Classification Search .................. 324/220, 324/219, 228–229, 232–234, 236–243
See application file for complete search history.

(56) References Cited

U.S. PATENT DOCUMENTS

| 2,219,708 | A | * | 10/1940 | Kruse .............................. 33/542 |
| 3,483,466 | A | * | 12/1969 | Beaver et al. ................. 324/220 |
| 3,786,684 | A | * | 1/1974 | Wiers et al. ................... 73/866.5 |
| 4,330,748 | A | * | 5/1982 | Holden .......................... 324/225 |
| 4,675,604 | A | * | 6/1987 | Moyer et al. .................. 324/220 |

(Continued)

FOREIGN PATENT DOCUMENTS

CA  2592094  7/2006

(Continued)

OTHER PUBLICATIONS

Wiley, "Borehole Televiewer-Revisited", SPWLA Twenty-First Annual Logging Symposium, Jul. 8-11, 1980, pp. 1-16.*

(Continued)

*Primary Examiner* — Patrick Assouad
*Assistant Examiner* — Lamarr Brown
(74) *Attorney, Agent, or Firm* — Gable Gotwals

(57) ABSTRACT

A pipeline inspection tool includes two pole magnets oriented at an oblique angle relative to the central longitudinal axis of the tool body. An array of sensor coil sets is located between opposing edges of the two pole magnets and oriented perpendicular to the central longitudinal axis. Each sensor coil set includes a transmitter coil and two opposing pairs of receiver coils that are gated to receive reflections from the wall of a tubular member. Because the line of sensor coils is rotated relative to the magnetic bias field, the receiver coils are in-line with, and have the same angular orientation as, the transmitter coil. The tool provides improved sensitivity to small defects, substantial decrease in RF pulser power requirements, full circumferential coverage, self-calibration of the transmitted signals, and less interference between transmitter coils caused by acoustic ring around.

21 Claims, 8 Drawing Sheets

U.S. PATENT DOCUMENTS

| | | | |
|---|---|---|---|
| 4,691,572 A | | 9/1987 | van den Berg et al. |
| 4,789,827 A | * | 12/1988 | Bergander ............... 324/220 |
| 4,797,613 A | * | 1/1989 | Wentzell .................. 324/220 |
| 4,851,773 A | * | 7/1989 | Rothstein ................. 324/220 |
| 4,857,851 A | * | 8/1989 | Anderson et al. ......... 324/326 |
| 4,893,077 A | * | 1/1990 | Auchterlonie ......... 324/207.17 |
| 4,909,091 A | * | 3/1990 | Ellmann et al. ............ 73/866.5 |
| 4,952,875 A | * | 8/1990 | Adams et al. ............. 324/220 |
| 5,233,297 A | * | 8/1993 | Lara ........................ 324/220 |
| 5,256,966 A | * | 10/1993 | Edwards ................... 324/220 |
| 5,419,206 A | * | 5/1995 | Kamioka et al. ....... 73/862.333 |
| 5,454,276 A | | 10/1995 | Wernicke |
| 5,532,587 A | * | 7/1996 | Downs et al. .............. 324/220 |
| 5,565,633 A | | 10/1996 | Wernicke |
| 5,574,223 A | * | 11/1996 | Kiefer ........................ 73/623 |
| 5,581,037 A | * | 12/1996 | Kwun et al. ................. 73/623 |
| 5,619,423 A | | 4/1997 | Scrantz |
| 5,777,469 A | * | 7/1998 | Hockey et al. ............. 324/240 |
| 6,009,756 A | | 1/2000 | Willems et al. |
| 6,087,830 A | * | 7/2000 | Brandly et al. ............. 324/220 |
| 6,100,684 A | * | 8/2000 | Ramaut ...................... 324/220 |
| 6,404,189 B2 | | 6/2002 | Kwun et al. |
| 6,456,066 B1 | * | 9/2002 | Burd et al. .................. 324/220 |
| 6,628,118 B1 | * | 9/2003 | Amini ......................... 324/334 |
| 6,820,653 B1 | | 11/2004 | Schempf et al. |
| 6,967,726 B2 | * | 11/2005 | King et al. .................. 356/630 |
| 6,975,120 B2 | * | 12/2005 | Amini ......................... 324/339 |
| 7,084,623 B2 | * | 8/2006 | Imamoto et al. ............ 324/240 |
| 7,143,659 B2 | * | 12/2006 | Stout et al. ................. 73/865.8 |
| 7,256,576 B2 | * | 8/2007 | Mandziuk et al. .......... 324/220 |
| 7,356,421 B2 | * | 4/2008 | Gudmundsson et al. ...... 702/38 |
| 7,358,721 B2 | * | 4/2008 | Narishige et al. ........... 324/240 |
| 7,548,059 B2 | | 6/2009 | Thompson et al. |
| 7,683,611 B2 | * | 3/2010 | Burkhardt et al. ........... 324/220 |
| 7,782,048 B2 | * | 8/2010 | Sawawatari ................. 324/220 |
| 8,089,273 B2 | * | 1/2012 | Hoyt ........................... 324/220 |
| 2004/0095137 A1 | | 5/2004 | Kwun et al. |
| 2004/0207395 A1 | * | 10/2004 | Sarfaty et al. .............. 324/230 |
| 2004/0217759 A1 | * | 11/2004 | Burkhardt et al. .......... 324/220 |
| 2004/0221652 A1 | | 11/2004 | Flora et al. |
| 2004/0232909 A1 | * | 11/2004 | Imamoto et al. ............ 324/228 |
| 2005/0072237 A1 | | 4/2005 | Paige et al. |
| 2006/0027022 A1 | * | 2/2006 | Flora et al. ................... 73/627 |
| 2006/0158181 A1 | * | 7/2006 | Shoji .......................... 324/240 |
| 2007/0222436 A1 | | 9/2007 | Gao et al. |
| 2007/0229066 A1 | * | 10/2007 | Narishige et al. ........... 324/222 |
| 2008/0092672 A1 | | 4/2008 | Gibson et al. |
| 2008/0215257 A1 | | 9/2008 | Stripf et al. |
| 2009/0078048 A1 | | 3/2009 | Alers et al. |
| 2009/0139337 A1 | | 6/2009 | Owens et al. |
| 2009/0158850 A1 | | 6/2009 | Alleyne et al. |
| 2009/0193899 A1 | | 8/2009 | Panetta et al. |
| 2010/0117635 A1 | | 5/2010 | Hoyt |
| 2010/0199767 A1 | | 8/2010 | Ganin |

FOREIGN PATENT DOCUMENTS

| | | |
|---|---|---|
| DE | 102007058043 | 6/2009 |
| JP | 59058358 A | 4/1984 |
| JP | 60080760 | 5/1985 |
| JP | 60080760 A | 5/1985 |
| JP | 62067447 A | 3/1987 |
| WO | WO 2006/048290 | 5/2006 |
| WO | WO 2006/069684 | 7/2006 |

OTHER PUBLICATIONS

Simek et al., "In-Line Inspection EMAT Utilizing an Oblique Field", International NACE Corrosion Conference & EXPO 2012, pp. 1-9.*

Simek, "Oblique Field Magnetic Flux Leakage Survey Complements Axial Field Data", International NACE Corrosion Conference & EXPO 2011, pp. 1-9.*

Van Den Berg et al., "Development of an Electromagnetic Acoustic Transducer for Inspecting the Wall Thickness of Offshore Risers From the Inside, 1988,".

Netherlands Patent Office, "Search Report issued by the Netherlands Patent Office dated Dec. 16, 2010 in Patent Application No. 2004962,".

Austrian Patent Office, "First Office Action issued by the Austrian Patent Office dated Feb. 25, 2011 in Patent Application No. 10222010,".

Search Report issued by the United Kingdom Intellectual Property Office dated Aug. 10, 2010 in application GB1010491.7 (2 pgs).

Search Report issued by the United Kingdom Intellectual Property Office dated Aug. 25, 2010 in application GB1010493.3 (1 pg).

* cited by examiner

PIPELINE INSPECTION TOOL WITH DOUBLE SPIRAL EMAT SENSOR ARRAY

REFERENCE TO PENDING APPLICATIONS

This application claims the benefit of U.S. Provisional Patent Application No. 61/230,879, filed Aug. 3, 2009, and U.S. Non-Provisional patent application Ser. No. 12/572,752, filed on Oct. 2, 2009, which in turn claimed priority to U.S. Provisional Patent Application No. 61/220,734, filed Jun. 26, 2009.

FIELD OF INVENTION

This invention relates generally to inspection tools designed to detect anomalies in tubing, piping and pipelines and, more particularly, to inline inspection tools employing magnetic flux leakage detection techniques.

BACKGROUND OF THE INVENTION

Many installed pipelines may be inspected using the Magnetic Flux Leakage (MFL) technique, primarily for the purpose of identifying metal loss anomalies. Magnetic flux leakage has been shown to respond in predictable ways to anomalies in the wall of the pipeline as the principal axis of the metal loss anomaly and field angle are varied. Both experimental and modeling results have been used to confirm this effect, which is also widely described in the literature.

Due in part to limitations imposed by data acquisition, data storage and magnetic circuit designs, most in-line inspection tools have employed axially oriented magnetizers (see e.g., U.S. Pat. No. 6,820,653 to Schempf et al.). However, the present axial field magnetizer designs make identification and quantification of extremely narrow axial features difficult, or in some cases, impossible. For these feature classes, a solution using a magnetic field in the circumferential or transverse direction, have been marketed and placed in service over the past decade by pipeline inspection providers. However, due to the constraints of physics, the performance and accuracy of these transverse magnetic flux inspection (TFI) tools in general is less than that of axial field tools for general metal loss anomalies.

Additionally, these TFI tools typically require a minimum of two magnetizer assemblies in order to achieve adequate coverage, making it impractical or difficult to incorporate these into an existing axial MFL tool.

For those pipelines that may have extremely narrow metal loss features, or certain classes of seam weld anomalies, standard axial field tools do not provide adequate detection and quantification capabilities. In these cases, for MFL based tools, either the initial or supplemental surveys are performed using a TFI tool. While TFI tools may be capable of detecting extremely narrow anomalies and certain seam weld anomalies, they also detect all of the remaining volumetric metal loss features typically found in pipelines, complicating the process of identifying the targeted anomaly classes.

One of the earliest TFI arrangements is described in U.S. Pat. No. 3,483,466 to Crouch et al. Crouch discloses a pair of electromagnets arranged perpendicular to each other with detectors such as magnetometers or search coils positioned on each side of the magnets. Other than the use of permanent magnets and hall device-type sensors, Crouch's arrangement remains as the basis for most modern implementations. Additionally, some designs involve segmented or individual discrete magnets that, in most cases, retain the transverse or circumferential field direction. For example, U.S. Pat. No. 3,786,684 to Wiers et al. discloses individual magnets arranged in arrays oblique to the pipe axis with the fields of each array perpendicular the others. However, this arrangement limits the field to sections and areas between the poles of each individual magnet. Furthermore, the short pole spacing required for a Wiers-type implementation decreases the length of the magnetic circuit, thereby causing the tool to suffer from velocity effects, and also masks, distorts or degrades data quality at welds, dents, or other anomalies.

Other designs involve elaborate complex geometries, multiple magnetizer sections, and elaborate mechanical arrangements such as helical drives, gears and wheels designed to induce spiral or helical motion of the magnetizer section. For example, U.S. Pat. No. 5,565,633 to Wernicke discloses a mechanically complicated device for use with magnetizer sections having two or more magnetic circuits and a plethora of sensing units. In one embodiment, the magnet blocks are arranged with spirally situated parallel poles. In another embodiment, the magnet blocks are twisted pole pairs displaced axially. Both embodiments require mechanically induced rotation in order to achieve full coverage of the inner pipe surface. Similar to Wernicke, U.S. Pat. No. 6,100,684 to Ramuat discloses a substantially transverse field magnetization arrangement that involves multiple magnetizer sections and a complex arrangement of wheels to induce helical motion of the sections and achieve overlapping or full coverage of the pipe wall. U.S. Pat. No. 7,548,059 to Thompson et al. includes two skids (poles) that incorporate fixed magnets arranged in closely spaced pairs to create a nominally transverse field spiraling around the pipe. This tool—which includes a variety of moving parts such as supporting tendons, pulleys, and springs—requires much added complexity in order to be flexible enough to accommodate bends in the pipeline. Furthermore, the magnets in this arrangement induce a field between two parallel poles, forming a single closed loop circuit between the poles of the individual discrete magnet blocks.

Similar to Thompson et al., the magnets used in the prior art are described as being blocks, with no reference to a supple or conformable upper surface used for the magnet block. Use of a rigid contact arrangement for the magnetic circuit degrades data quality by introducing air gaps or variable reluctance zones in the magnetic field path at dents or along welds and other upsets that may be present within the pipeline. For certain classes of features, disturbances created in the ambient field mask or otherwise distort the flux leakage signals present because of the features of interest. Any magnetic anomalies existing within dents and weld zones are of greater significance due to their presence within these zones and, as such, represent areas in which data quality is critical.

Additionally, the prior art requires the use of a large number of poles or surfaces in an intimate contact arrangement to the pipe wall surface. This arrangement can result in extremely high frictional forces or resistance to motion being experienced by the magnetizer assembly, thereby inhibiting or preventing its use in applications requiring lower friction.

As already discussed, pipeline operators are currently able to inspect many installed pipelines using the magnetic flux leakage (MFL) technique, primarily for the purpose of identifying metal loss anomalies. However, for certain classes of anomalies, the current axial field magnetizer designs used in the MFL technique make detection and quantification of extremely narrow, crack or crack-like axial features difficult or, in some cases, impossible. To enable detection and quantification of these features, alternative techniques utilizing acoustic (ultrasonic) waves have been studied or employed.

These acoustic waves are typically generated by external piezoelectric transducers or electro-magnetic acoustic transducers (EMAT).

EMAT implementations are usually one of two basic types: Lorentz and magnetostrictive. Both types require an external magnetic bias field to be present. In Lorentz-type EMAT, the magnetic bias field is perpendicular to the pipe wall and interacts with Eddy current-induced paths or strains in the pipe wall. The magnetostrictive-type EMAT uses a magnetic bias field that is in the pipe wall plane, axial or circumferential, and interacts with magnetically induced strains.

It is well known in the nondestructive testing industry that magnetostriction in steel is much more efficient in generating shear horizontal (SH) acoustic waves when the magnetic bias field is at an angle with respect to the sensor coil conductors of the EMAT. This result has been verified by the inventors during initial development of an EMAT sensor array according to the invention disclosed herein. During the study it was discovered that several of the notches machined into test plates were not detectable using an axially oriented magnetic bias field. Rotating the magnetic bias field angle relative to the axis of travel and the EMAT sensor provided an increase of approximately 20 decibels in measured signal. This arrangement produced a much greater signal response compared to the electronic noise, resulting in distinct crack indications above a relatively uniform baseline.

Consequently SH wave applications using EMAT sensor coils that are set at an angle to the magnetic field, are usually superior to applications where the field plane lines are parallel to the sensor coil conductors (see e.g. DE Pat. App. Pub. No. 10/2007/0058043 assigned to Rosen Swiss AG). Detection and quantification of stress corrosion cracking (SCC) is one of the main types of anomalies targeted by this technique. In addition to SCC, which is typically axially oriented, girth welds, which are circumferentially oriented, have been known to exhibit crack-like features. Therefore, for an EMAT system to be globally effective, a method is needed that is readily adaptable for detection of both axially and circumferentially oriented features.

Prior art in-line inspection tools use annular arrays of permanent magnets to magnetize the pipe in a direction that is parallel to the axis of the pipe. To obtain the beneficial angle between the magnetic bias field and the sensor coils, the sensor coils are rotated toward the pipe axis (see e.g., Canadian Pat. Appl. No. CA 2,592,094 of Alers et al.). The SH waves impinge on the plane of the axially oriented SCC at this same angle. Therefore, SH wave reflections from SCC are detected efficiently only by receiver sensor coils that are positioned lateral to and rotated toward the transmitter coil. Also, the attenuation measurements used for detection of coating disbond use receiver coils that are positioned diagonally to and rotated toward the transmitter coils. These attenuation receiver coils are shifted circumferentially so that they are in-line with the transmitted wave. An appreciable increase in received signal amplitude is an indication a coating disbond.

There is a need for an EMAT tool that provides full coverage of the inner pipe wall surface without the need for mechanically complicated structures and produces a field that may be used with EMAT sensors to detect axially- or circumferentially-oriented volumetric features and coating disbonds.

SUMMARY OF THE INVENTION

A pipeline inspection tool made according to this invention includes at least two pole magnets arranged about an external surface of the tool body and oriented oblique to the central longitudinal axis of the tool body. A sensor array is provided between the opposing edges of the two pole magnets. The sensor array includes a line or set of sensor coils that are oriented at a different angle than the pole magnets relative to the longitudinal axis of the tool body. Therefore, the sensor array is at an angle with respect to the magnetic bias field generated by the pole magnets. The pole magnets and the sensor array may each extend the length of the tool body and have a general helical-shape. Preferably, the sensor coil sets are perpendicular to the longitudinal axis of the tool body but, depending on the type of anomaly to be detected, may be arranged parallel to the longitudinal axis of the tool body.

Each sensor coil set may lie 180° opposite a corresponding sensor coil set, with a portion of the opposing sensor coil sets contained within a common circumferential band of the tool. Sensor coil sets lying on a same side of the tool body are offset from one another, being generally evenly spaced apart and equidistant from the opposing edges of the oblique-oriented pole magnets. Each set of sensor coils includes at least one transmitter coil and at least two opposing pairs of receiver coils. One receiver coil in each pair may be a RD receiver coil and the other receiver coil may be a RA receiver coil. Because the sensor coil sets are rotated relative to the magnetic bias field, the receiver coils are in-line with, and have the same angular orientation as, the transmitter coil. In other words, the receiver coils are oriented parallel to the transmitter coil and do not need to be shifted diagonally or rotated with respect to the transmitter coil.

The transmitter coil transmits a tone burst or signal that impinges upon the wall of the tubular member being inspected and travels back to the receivers. The receiver coils are spaced relative to the transmitter coil so that the signal transmitted by the transmitter coil does not mask detection of the reflected signal by the receiver coils. Each receiver coil is gated to receive these reflected signals—which may be normalized—within a targeted sampling zone and detect anomalies in the tubular member. The transmitter may then transmit a second signal after the first signal has traveled a predetermined number of times around the circumference of the tubular member. Depending on the orientation of the sensor coil sets relative to the oblique-oriented magnets, the sensor array is capable of detecting wall anomalies in both the axial and circumferential direction.

It is an object of this invention to provide a magnetic flux leakage (MFL) tool that responds to a broad range of anomalies capable of generating magnetic flux leakage signals. Another object of this invention is to provide a MFL tool capable of 360° coverage of the internal pipe wall using a single magnetizer without the need for multiple magnetizer sections, magnetizers, or relative motion between the sensors or sections to achieve detection of nominally axially oriented features. It is another object of this invention to provide a MFL tool with an EMAT array that reduces the probability of missing cracks in the pipe wall and has improved sensitivity to small defects, i.e., up to 20 db increase in signal amplitude. Yet another object of this invention is to provide an EMAT array that requires a substantial decrease in RF pulser power requirements. Still yet another object of this invention is to provide an EMAT array that includes self-calibration of the transmitted signals using the receiver coils closest to transmitter coils. A further object of this invention is to provide an EMAT array that experiences less interference between transmitters caused by acoustic ring around.

DETAILED DESCRIPTION OF THE PREFERRED EMBODIMENTS

Figure 1:
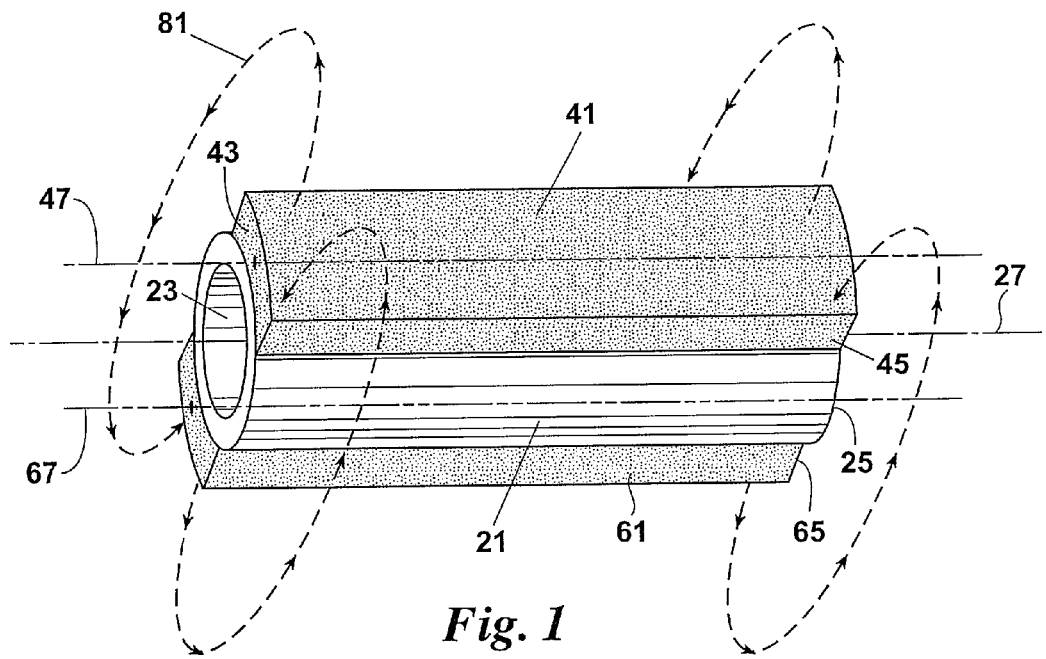
FIG. 1 is an isometric view of an axially oriented magnetizer design. The direction of the magnetic field is circumferential or transverse to the longitudinal axis of the pipe.
Figure 2:
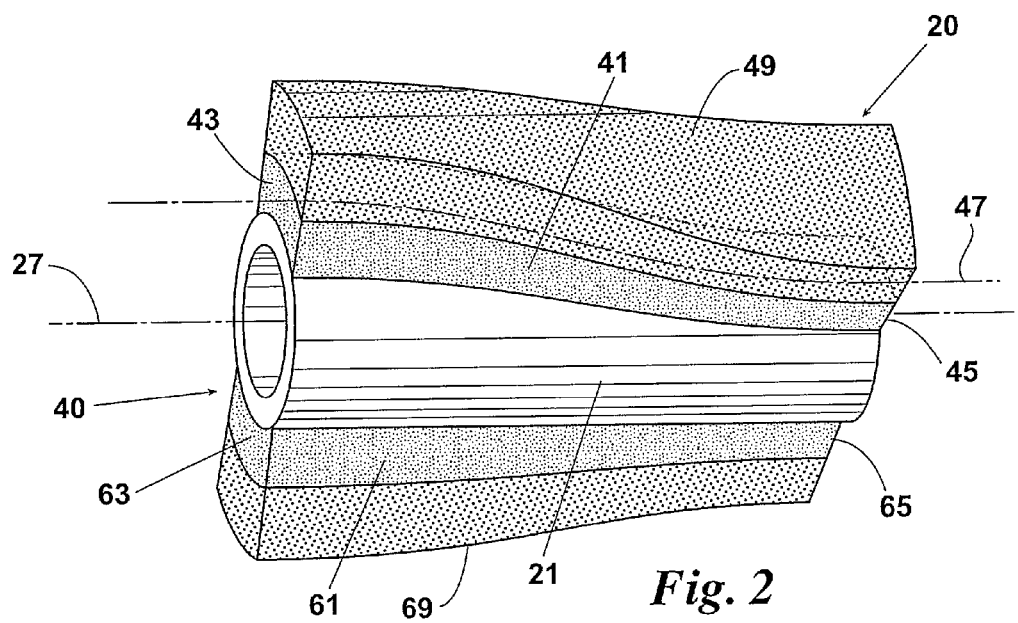
FIG. 2 is an isometric view of an embodiment of an oblique magnetizer assembly according to this invention that utilizes a spiral magnet pole design. The pole magnets are rotated or spiraled about 30° and include a flexible or conformable upper surface.
Figure 3:
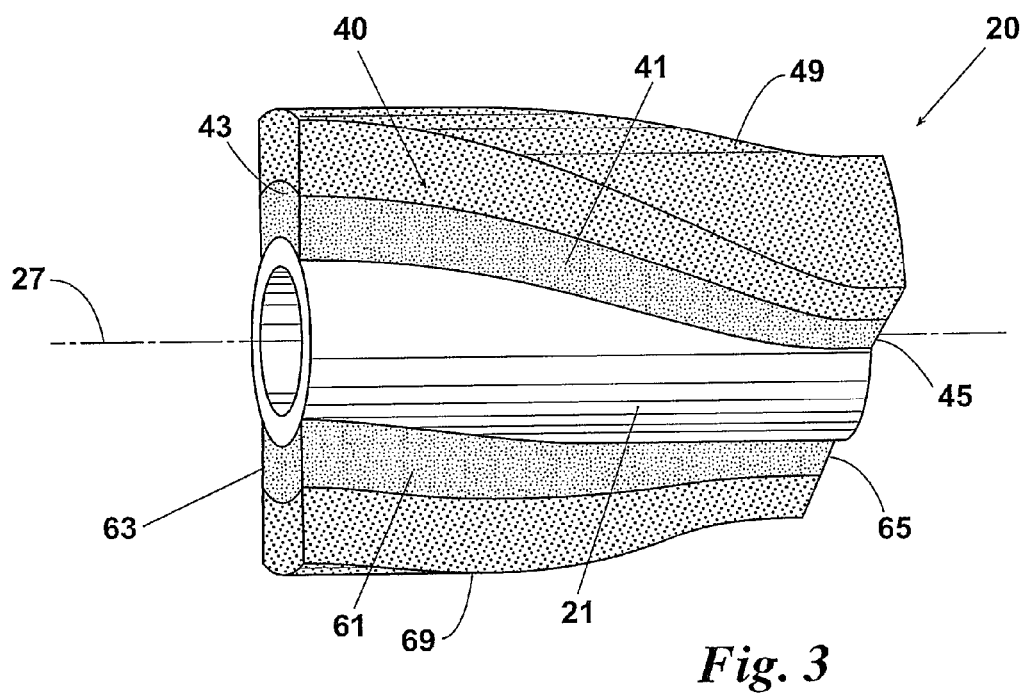
FIG. 3 is a view of another embodiment of the oblique magnetizer assembly in which the pole magnets are rotated about 60°.
Figure 4:
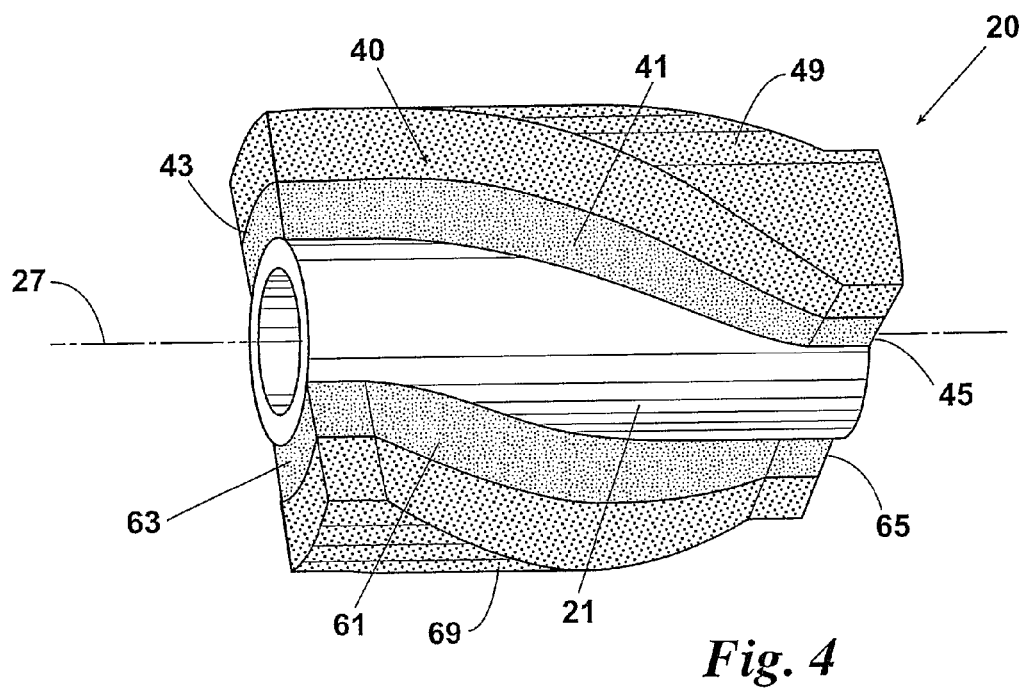
FIG. 4 is a view of yet another embodiment of the oblique magnetizer assembly in which the pole magnets are rotated about 90°.
Figure 5:
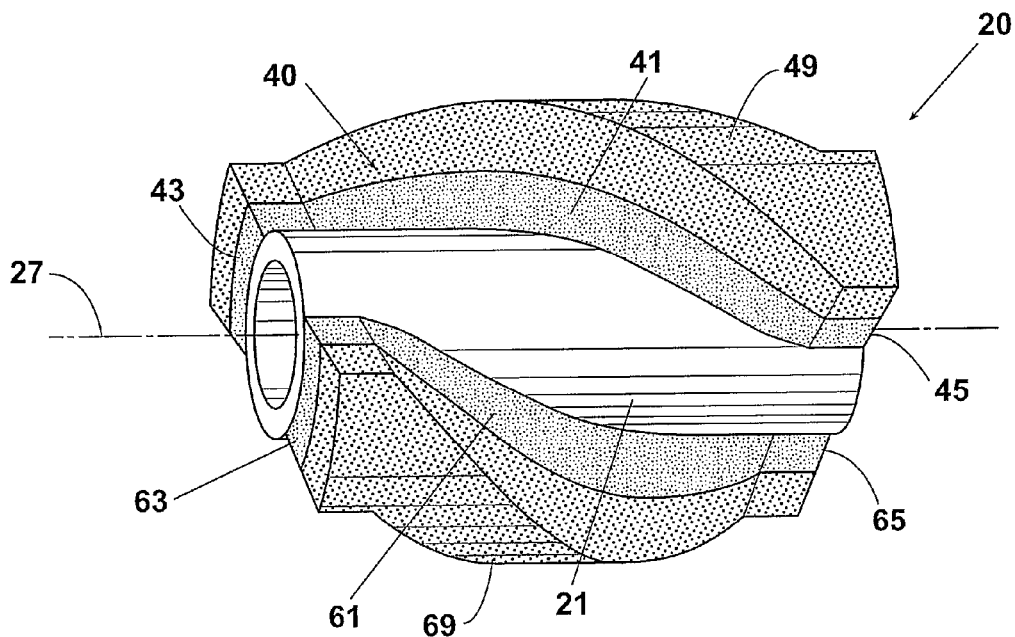
FIG. 5 is a view of still yet another embodiment of the oblique magnetizer assembly in which the pole magnets are rotated about 120°.

Preferred embodiments of a magnetic flux leakage (MFL) tool made according to this invention will now be described by making reference to the drawings and the following elements illustrated in the drawings:

10 In-line inspection tool
20 MFL tool/oblique magnetizer
21 Cylindrical tool body
23 First end of 21
25 Second end of 21
27 Longitudinal axis of 21
31 Radial disc
40 Magnetic circuit
41 Pole magnet
43 First end of 41
45 Second end of 41
47 Longitudinal centerline of 41
49 Conformable upper surface
51 Brushes
61 Pole magnet
63 First end of 61
65 Second end of 61
67 Longitudinal centerline of 61
69 Conformable upper surface
71 Brushes
80 Magnetic field
81 Magnetic flux path of field 80
90 Sensor array
91 First end of 90
93 Second end of 90
94 Sensor coil line or set of 95, 97 & 98
95 Transmitter coil
96 Shear horizontal wave generated by 95
97 RD receiver coil
98 RA receiver coil
99 Central axis of sensor coil set 94
100 Axial magnetizer
110 Deformation sensing section Referring first to FIG. 1, a north pole magnet 41 and a south pole magnet 61 are arranged about 180° opposite one another on a cylindrical tool body 21 so that the respective longitudinal centerline 47, 67 of each pole magnet 41, 61 is parallel to the longitudinal centerline 27 of the cylindrical tool body 21 (and therefore parallel to a central longitudinal axis of the pipe being inspected). Although pole magnets 41, 61 differ from prior art implementations in that, for example, each magnet 41, 61 extends along the entire length of the cylindrical body 21, their axial orientation as illustrated here is typical of prior art implementations. Arranged in this way, pole magnets 41, 61 generate a circumferential or transverse magnetic field relative to the pipe wall—as illustrated by magnetic flux paths 81—and multiple magnetizer sections are required to provide complete coverage of the internal wall surface of the pipe.

Referring now to FIGS. 2 to 6, an oblique magnetizer assembly 20 according to this invention includes a magnetic circuit 40 that has two spiraled pole magnets 41, 61 arranged about 180° opposite one another on cylindrical tool body 21. Each pole magnet 41, 61 extends between a first end 23 and second end 25 of the cylindrical tool body 21. Additional pairs of spiraled pole magnets 41, 61 may also be employed, with each spiraled pole magnet 41 or 61 extending between the ends 23, 25 of cylindrical tool body 21 and spaced 360°/n from its adjacent and opposite pole magnet 61, 41 ("n" being an equal to the number of pole magnets 41, 61 employed). The pole magnets 41, 61 preferably have a flexible or conformable upper surface 49, 69, respectively, that helps reduce friction forces and minimize velocity effects as the oblique magnetizer assembly 20 travels through the interior of a pipe. The conformable upper surface 49, 69 also allows the magnetizer assembly 20 to compress a sufficient amount in order to pass by internal obstructions, bends, and reductions in the pipe that might otherwise damage the magnetizer assembly 20 or slow or prevent its passage.

Figure 6:
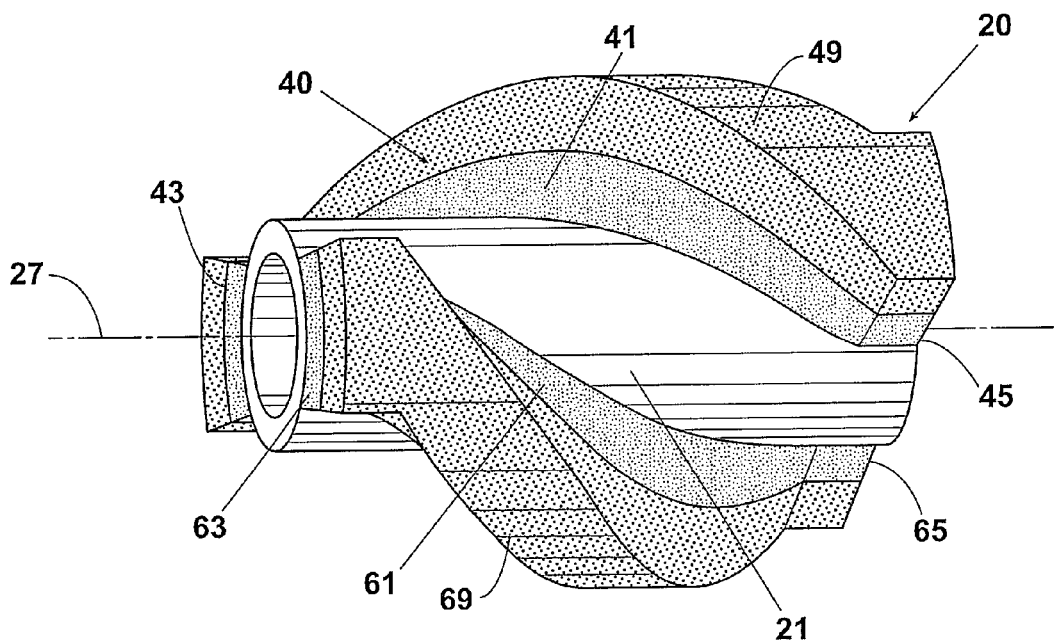
FIG. 6 is a view of yet another embodiment of the oblique magnetizer assembly in which the pole magnets are rotated about 150°.
Figure 7:
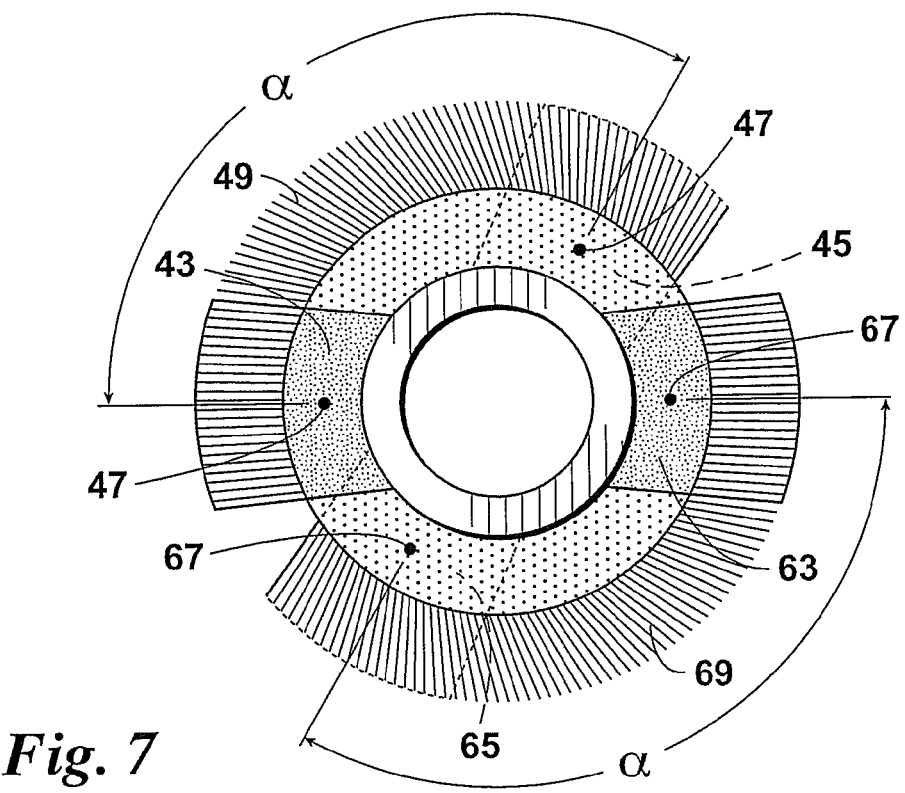
FIG. 7 is an end view of another embodiment of the oblique magnetizer assembly, illustrating the relationship between the two ends of the spiraled or rotated pole magnets. In this example, the pole magnets are rotated about 135°. The conformable upper surface of each pole magnet includes a bristle or brush-type surface.

The rotation amount of the pole magnets 41, 61 depends on the amount of rotation required to achieve full coverage of the internal pipe wall surface. Going through the sequence from FIG. 2 to FIG. 6, the pole magnets 41, 61 are each rotated or spiraled in incremental amounts, for a nominal rotation of about 150 degrees (as illustrated in FIG. 6). When rotated, the second end 45, 65 of the pole magnet 41, 61 is offset by a predetermined angle or amount α relative to its respective first end 43, 63 (see FIG. 7). Because of this rotation amount α, the respective longitudinal centerline 47, 67 of each spiraled pole magnet 41, 61 is non-parallel to the central longitudinal axis 27 of the cylindrical tool body 21. The rotation of pole magnets 41, 61 also helps induce a sufficient amount of rotation of magnetizer assembly 20 as it travels through the interior of the pipe.

Figure 8:
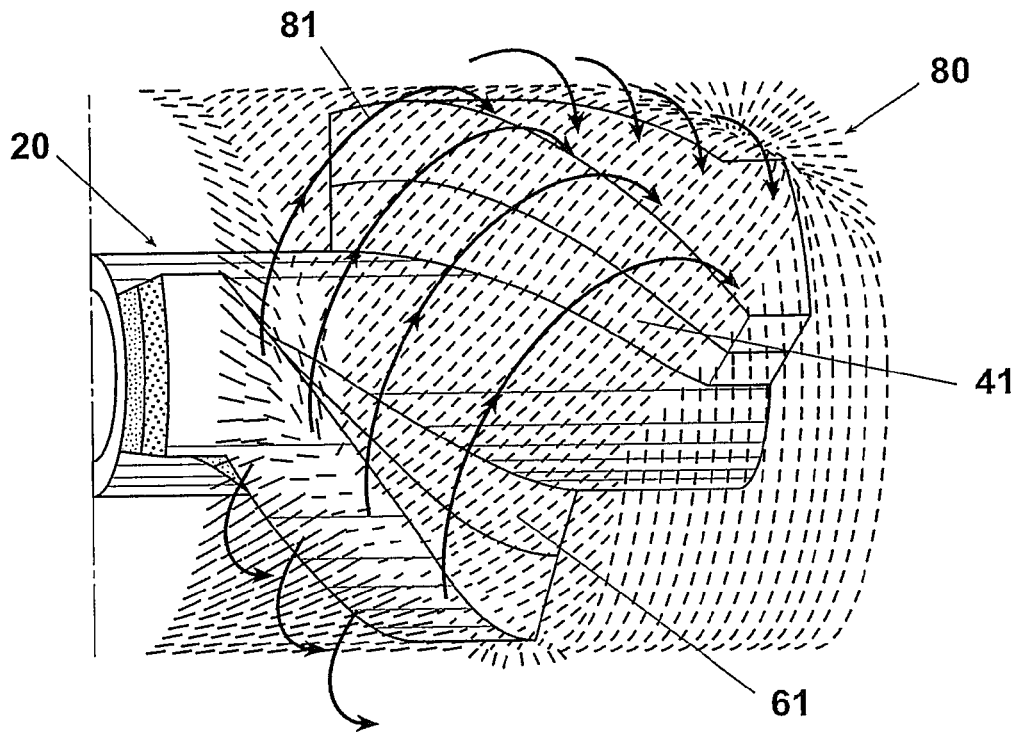
FIG. 8 illustrates field results from the oblique magnetizer arrangement. The field direction is diagonal, or oblique, to the longitudinal axis of the pipe.

FIG. 8 illustrates the magnetic field 80 generated from a prototype of oblique magnetizer assembly 20, which was configured similar to the magnetizer assembly 20 shown in the rotation sequence of FIGS. 2 to 6. Unlike prior art in-line inspection tools, the direction of magnetic field 80 is diagonal or oblique to the pipe axis rather than circumferential or transverse, with magnetic flux paths 81 emanating from the poles 41, 61 and traveling in opposite directions to reach a corresponding pole 61, 41. The magnetic flux lines 81 generated by each pole magnet 41, 61 are guided to the path of least resistance: into the pipe wall and toward the adjacent pole magnet 61, 41. The angle of the magnetic field 80 is generally perpendicular to the flux lines 81 formed by the magnetic poles 41, 61 and generally parallel to a line forming the shortest distance between the magnet poles 41, 61. The direction of magnetic field 80 within the extents of poles 41, 61 may range from 30 to 60 degrees relative to the pipe axis.

Figure 9:
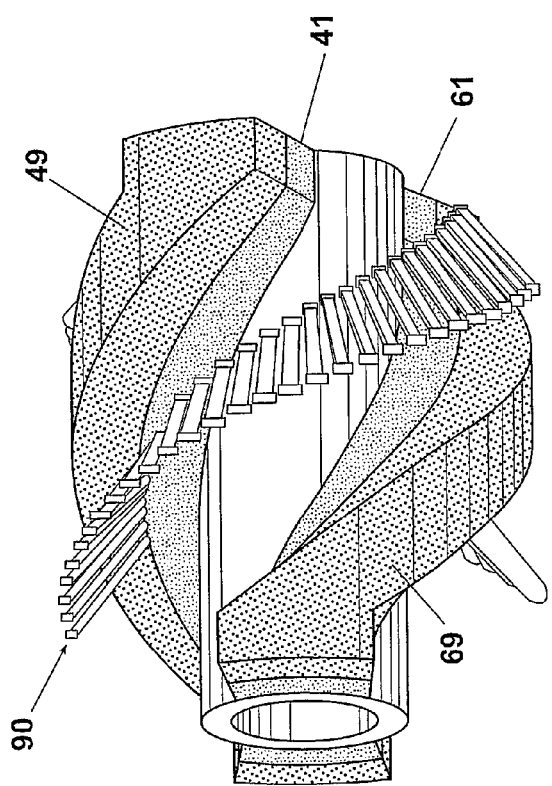
FIG. 9 is a view of an embodiment of the oblique magnetizer assembly that includes a helical-shaped sensor array mounted from one end of the magnetizer to the other, providing complete coverage of the internal pipe wall surface and incorporating a degree of overlap to accommodate any tool rotation that may take place.
Figure 10:
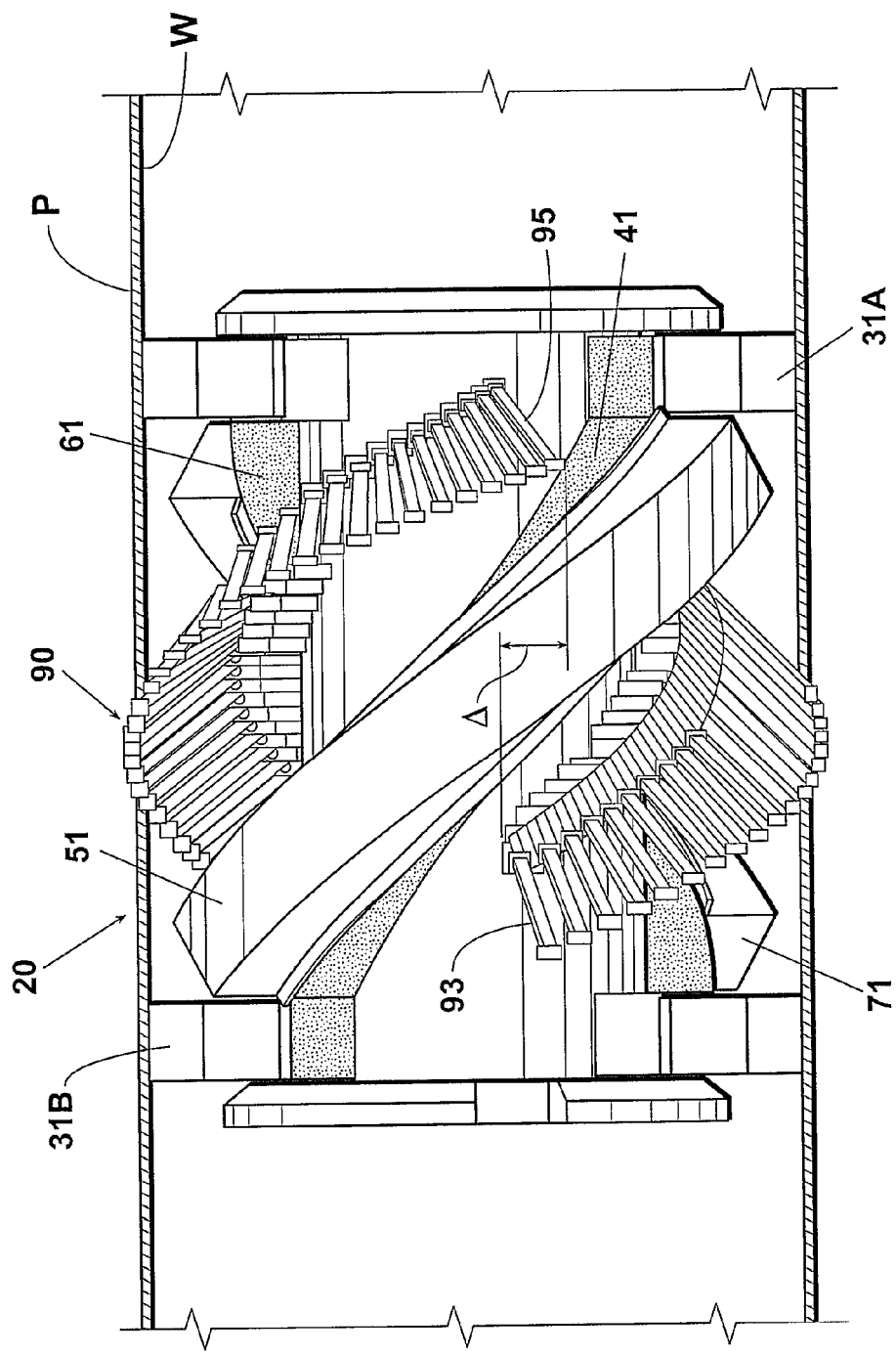
FIG. 10 is a view of the oblique magnetizer assembly of FIG. 8 encased in a pipe section.

Referring now to FIGS. 9 & 10 oblique magnetizer assembly 20 may include a helical-shaped sensor array 90 located substantially equidistant between rotated pole magnets 41, 61 and arranged to provide complete coverage of the internal wall surface W of pipe P and accommodate any rotation of magnetizer assembly 20 that may take place. The individual sensors in sensor array 90 may be of a kind well-known in the art for detecting magnetic flux leakage signals. Sensor array 90 preferably extends between the first end 23 and second end 25 of cylindrical body 21 (and therefore between the respective ends 43, 45 and 63, 65 of pole magnets 41, 61) and incorporates a degree of overlap Δ between a first end 91 and second end 93 of sensor array 90. The conformable upper surfaces 49, 69 of the pole magnets 41, 61 (see e.g. FIG. 6) may be in the form of brushes 51, 71. Radial discs 31A & B help propel and center magnetizer assembly 20 as it moves forward in pipe P under differential pressure.

Figure 11:
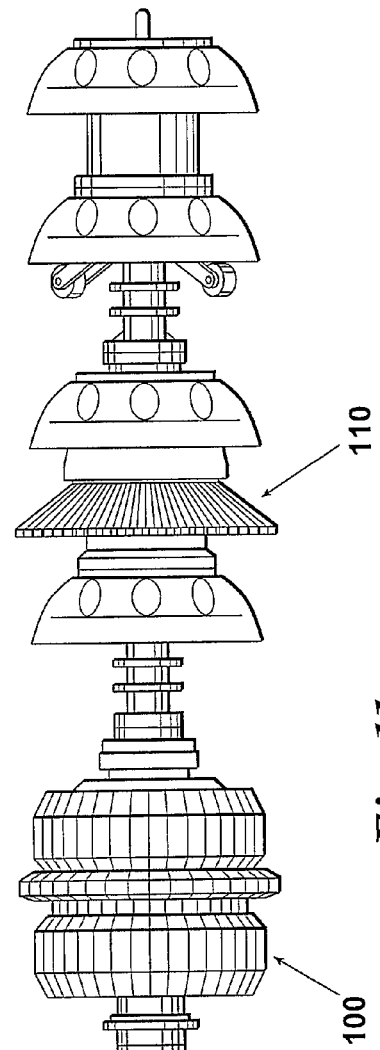
FIG. 11 is a view of an inline inspection tool that includes the oblique magnetizer assembly, an axial magnetizer and a deformation sensing section.

The final configuration of oblique magnetizer assembly 20 may include any current combination of data sets, including but not limited to deformation, high level axial MFL, internal/external discrimination, inertial data for mapping, and low level or residual MFL. In one preferred embodiment of an inline inspection tool 10 incorporating oblique magnetizer assembly 20, the tool 10 includes an axial magnetizer 100 and a deformation sensing section 110 (see FIG. 11).

Figure 12:
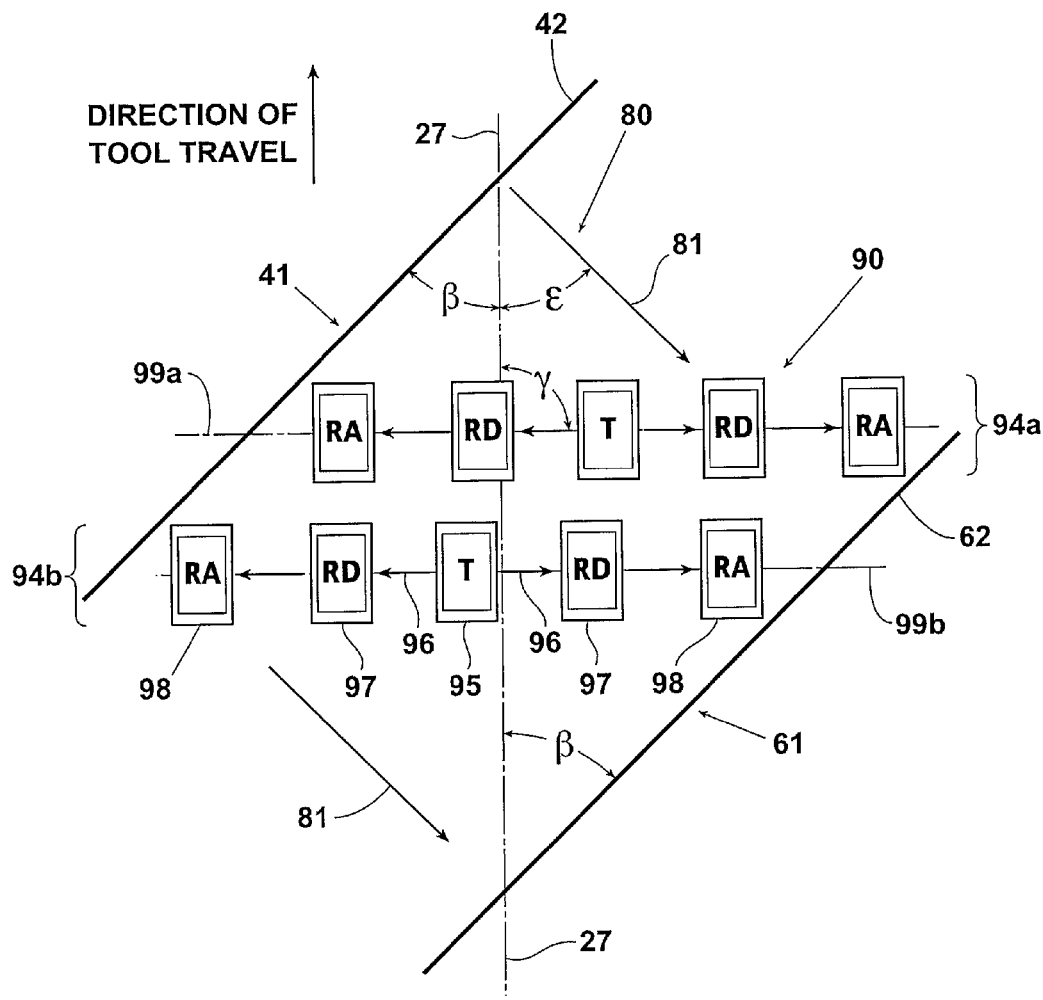
FIG. 12 is a schematic illustrating one side of a sensor array that includes two lines or sets of EMAT sensor coils located between two oblique-oriented pole magnets. Each sensor coil set includes two pairs of receiver coils and a transmitter coil located in-between the pairs of receiver coils. The sets are aligned perpendicular to the central longitudinal axis of the inline inspection tool (and, therefore, perpendicular to the central longitudinal axis of the tubular member being inspected) and each coil in the set shares a common centerline with the other coils in the set.
Figure 13:
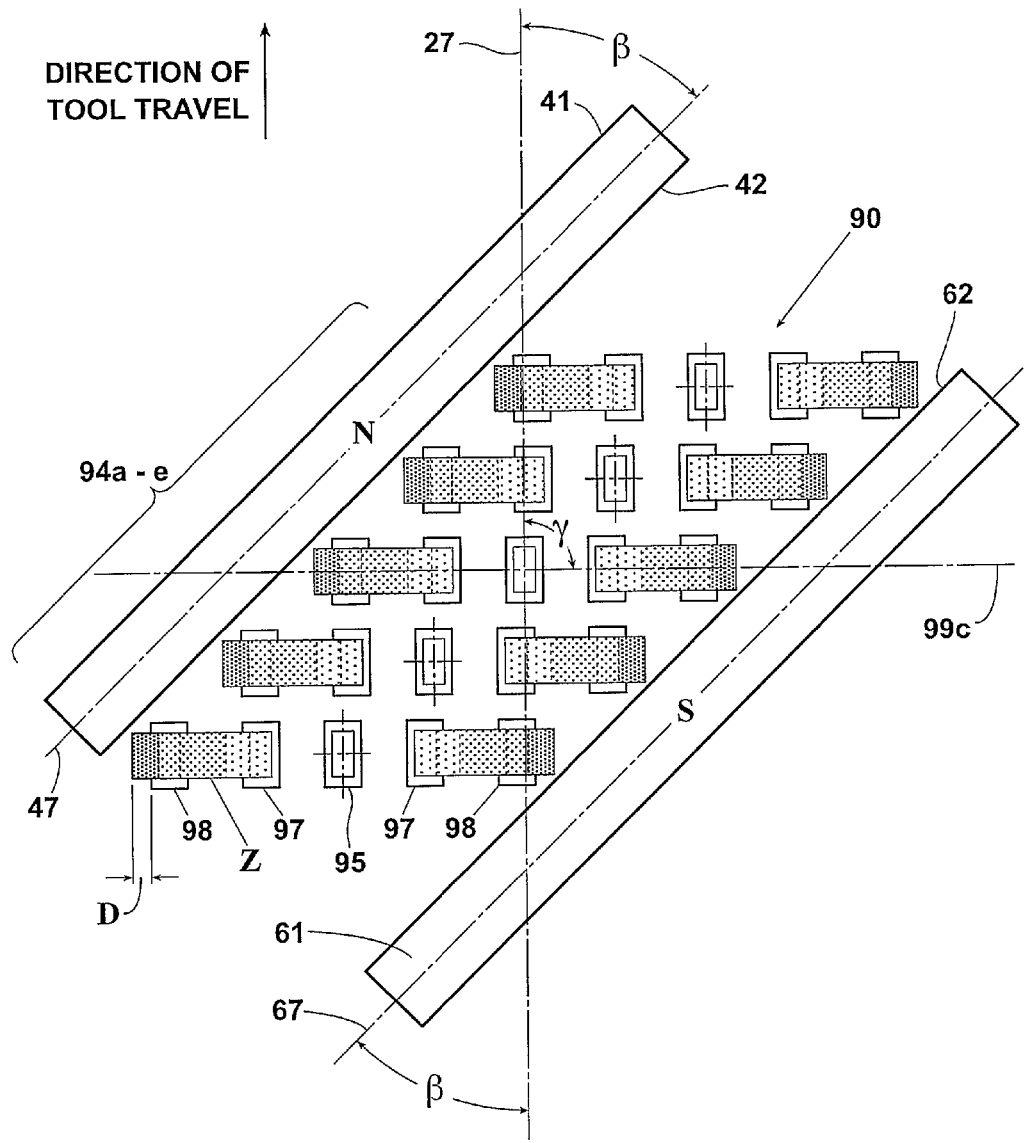
FIG. 13 is a view of one side of a sensor array having the EMAT sensor coil arrangement of FIG. 12 as applied to a 24 inch diameter tubular member.

Referring now to FIGS. 12 & 13, sensor array 90 includes electro-magnetic acoustic transducers (EMAT) sensor coils 95, 97 & 98 located between the opposing edges 42, 62 of the oblique-oriented permanent pole magnets 41, 61. The sensor coils 95, 97 & 98 are preferably arranged in sensor coil lines or sets 94a-e as defined by a respective sensor coil set central axis 99a-e. Each central axis 99a-e is generally parallel to the other axes 99a-e and oriented at a predetermined angle γ relative to the central longitudinal axis 27 of cylindrical tool body 21. A substantially identical set of sensor coil sets (not shown) to sensor coil sets 94a-e is arranged on the opposing external surface of cylindrical tool body 21, about 180° opposite sensor coil sets 94a-e.

The oblique-oriented pole magnets 41, 61 are generally at an angle β relative to central longitudinal axis 27, with angle β being different than angle γ. Because the flux lines 81 generated by pole magnets 41, 61 are generally perpendicular to the edges 42, 62 of the pole magnets 41, 61, magnetic field 80 is rotated at an angles relative to the central longitudinal axis 21 and, therefore, is at an angle with respect to sensor coil sets 94a-e. In a preferred embodiment, angle γ is about 90°, angle β is about 45°, and angles ε is about 45°.

Arranging the sensor coil sets 94a-e perpendicular to the central longitudinal axis 27 of cylindrical tool body 21 (and therefore perpendicular to the pipe axis) allows sensor array 90 to detect features in both the axial and circumferential directions. Transmitter coils 95 generate SH waves 96 that travel circumferentially around the pipe and impinge at a normal angle (perpendicular) to axially oriented cracks. Arranging the sensor coil sets 94a-e parallel to the central longitudinal axis 27 of the cylindrical tool body 21 (and therefore parallel to the pipe axis) allows sensor array 90 to detect features in the circumferential direction. Shear horizontal waves 96 are transmitted along the pipe wall in the axial direction so that reflections from transverse cracks, such as cracks in girth welds, are detected. Unlike the orientation of receivers in prior art EMAT tools, receiver coils 97, 98 do not have to be shifted diagonally with respect to, or rotated toward, the transmitter coil 95 in order to gain the benefits of having magnetic field 80 rotated with respect to the EMAT sensor coils 95, 97 & 98.

Sensor coils 95, 97 & 98 may be mounted on a suitable mechanism such as a spring loaded pads (not shown) that keep the coils 95, 97 & 98 in close proximity to the inside diameter of the pipe. The transmitter coils 95 induce SH guided waves 96 in two circumferential directions around the pipe. The receiver coils 97 detect reflections from stress corrosion cracks (SCC) and serve as the calibration receivers. Receiver coils 98 detect the SH guided waves 96 that propagate from the transmitter coils 95 in the circumferential direction. The characteristic features of these detected signals, such as amplitude and time of arrival, can be used to detect features such as coating disbond, corrosion and SCC.

The receiver coils 97, 98 are placed at a predetermined distance from transmitter coil 95 so that signal responses are detected by receiver coils 97, 98 but not affected adversely by the initial electronic excitation pulse. Each transmitter coil 95 in a set 94a-e is grouped with two receiver coils 97, 98 on each side. Sensor array 90 preferably includes the requisite number of transmitter coils 95 and receiver coils 97, 98 in order to provide overlapping coverage of SCC and coating disbond detection. In one preferred embodiment, each of two sensor arrays 90—arranged opposite one another and for use in a 24-inch diameter pipe—included five transmitter coils 95 and 20 total receiver coils 97, 98.

Each transmitter coil 95 when fired causes SH guided waves 96 to propagate to both to the left and to the right of the coil 95 and around the circumference of the pipe. The receiver coils 97, 98 closest to the active transmitter coil 95 are first sampled in time (gated) to receive the outgoing waves 96 and then gated at a longer predetermined time delay, preferably on the order of 50 and 90 microseconds for a 24-inch diameter pipe, to detect reflections from SCC. These reflections are from targeted sampling zones "Z" located between the RD receiver coils 97 and a predetermined distance "D" past the RA receiver coils 98 so as to maximize coverage and minimize interference. The reflection signals are normalized, i.e., divided by the outgoing signals detected in the RD receivers 97 to provide continuous calibration of the signal reflections.

By way of example, considering a 24-inch pipe and a target axial sample spacing of 6 mm (0.24 in.), a pulse rate of 390 Hz will yield an axial resolution of 5.1 mm (0.20 in.). This pulse rate allows the SH wave 96 to travel approximately 4.25 times around the pipe circumference before the second pulse or tone burst is fired. Consequently, the remnants of the first pulse are between the receiver coils 97, 98 and therefore have no affect on the receiver coils 97, 98 located on the opposite side of tool body 21 within that circumferential ring at the sampling time interval (gate).

The SH waves 96 are still within the receiver gates during the third tone burst, after the wave 96 has traveled about 8.5 times around the pipe. Using an attenuation factor of 0.8 in 2 feet of travel (a factor determined from lab experiments), a tone burst transmitted at 100 percent full scale has an amplitude of less than 0.3 percent when it arrives at the receiver coils 97, 98 located on the opposite side of the cylindrical tool body 21. This amount of noise is usually negligible compared to other sources of noise, e.g., thermal electronic noise, which can be as much as 3 percent of full scale.

Coating disbond is detected in the targeted sampling zones Z between RD receiver coils 97 and RA receiver coils 98 which are located in-line with the transmitter coils 95. Coating disbond detection may be accomplished by computing the ratio of the gated receiver signals. Ratios that are above a set threshold indicate a lack of coating or disbond on the pipe in a particular zone 99.

In studies conducted by the inventors, a sensor array 90 made according to this invention has shown the following benefits over the prior art:
- improved sensitivity to small defects, i.e., up to 20 db increase in signal amplitude;
- substantial decrease in RF pulser power requirements;
- full circumferential inspection coverage, reducing the probability of missing cracks;
- self-calibration of the transmitted signals using the receiver coils closest to transmitter coils; and
- less interference between transmitter coils caused by acoustic ring around.

Additional configurations are possible, depending upon the pipe diameter, with differing numbers of pole magnets 41, 61, sensor coils 95, 97 & 98 and sensor arrays 90. For circumferential detection, for example, the sensor array 90 would be rotated at an oblique angle $\gamma$ relative to the pipe axis, still being located within the angular magnetic biasing field 80. In addition to SCC and crack-like features, these configurations could respond to features such as coating disbonds and metal loss. The resulting system may also be used as an EMAT-only system or combined with any of the various other technologies available in in-line inspection tools, including but not limited to MFL, Deformation, Caliper, and Mapping.

While an EMAT tool that includes an oblique magnetizer and helical sensor array has been described with a certain degree of particularity, many changes may be made in the details of construction and the arrangement of components without departing from the spirit and scope of this disclosure. An EMAT tool according to this disclosure, therefore, is limited only by the scope of the attached claims, including the full range of equivalency to which each element thereof is entitled.

What is claimed is:

1. A sensor array for inspecting a wall of a tubular member, the sensor array comprising:
    a first and a second set of sensor coils, said first and second set of sensor coils each including a first and a second pair of receiver coils and a transmitter coil;
    said transmitter coil and said first and second pair of receiver coils each being arranged parallel to one another and sharing a common centerline, said transmitter coil being located between said first and second pair of receiver coils;
    wherein said common centerline is oriented at an angle $\gamma$ relative to a central longitudinal axis of an inspection tool on which each said set of sensor coils are mounted;
    the inspection tool having at least two pole magnets being arranged oblique to the central longitudinal axis of the inspection tool; and
    said first and second set of sensor coils each being located on an external surface of the inspection tool and lying between and substantially equidistant from opposing edges of the at least two pole magnets.

2. A sensor array according to claim 1 wherein said angle $\gamma$ is selected so that said common centerline is oblique relative to a central longitudinal axis of each pole magnet in the at least two pole magnets.

3. A sensor array according to claim 1 wherein said angle $\gamma$ is selected so that said common centerline is substantially parallel to the central longitudinal axis of the pipeline tool.

4. A sensor array according to claim 1 wherein said angle $\gamma$ is about 90°.

5. A sensor array according to claim 1 wherein the said first and second coil sensor sets are spaced apart from one another about 180°.

6. A sensor array according to claim 1 wherein a portion of said first sensor coil set and a portion of said second sensor coil set lie within a common circumferential band of the inspection tool.

7. A sensor array according to claim 1 wherein a portion of said transmitter coil in said first sensor coil set is offset from a portion of said transmitter coil in a direction perpendicular to the central longitudinal axis of the inspection tool.

8. A sensor array according to claim 1 wherein said transmitter coil in at least one of said first and second sensor coil sets transmits a signal, the signal being reflected by a wall surface of a tubular member being inspected by the inspection tool.

9. A sensor array according to claim 8 wherein the signal travels a predetermined number of times around a circumference of the tubular member before said transmitter coils transmits a second signal.

10. A sensor array according to claim 8 wherein at least one of said first and second pair of receiver coils samples the signal.

11. A sensor array according to claim 8 wherein at least one of said first and second pair of receiver coils samples the reflected signal.

12. A sensor array according to claim 11 wherein the reflected signal is a normalized signal.

13. A sensor array according to claim 11 wherein the sampling occurs at a predetermined sampling time interval.

14. A sensor array according to claim 11 wherein the signal travels a predetermined number of times around a circumference of the tubular member before at least one of said first and said second receiver coils samples the reflected signal.

15. A sensor array according to claim 11 wherein the sampling occurs within a targeted sampling zone, the targeted sampling zone extending between a first receiver coil and a predetermined distance "D" past a second receiver coil.

16. A sensor array according to claim 11 wherein each said first and second pair of receiver coils is spaced relative to said transmitter coil so that the signal transmitted by said transmitter coil does not mask detection of the reflected signal by said first and second pair of receiver coils.

17. A sensor array according to claim 1 further comprising said first and second pair of receiver coils each including a RD receiver coil and a RA receiver coil.

18. A sensor array according to claim 1 further comprising at least one receiver coil in said first and second pair of receiver coils being a gated receiver coil.

19. A sensor array according to claim 1 further comprising at least one receiver coil in each said first and second pair of receiver coils being a calibration coil.

20. A sensor array according to claim 1 further comprising at least one of said first and second sensor coil sets being capable of detecting at least one of an axially oriented wall anomaly and a circumferentially oriented wall anomaly.

21. A sensor array for inspecting a wall of a tubular member, the sensor array comprising:

a first and a second set of sensor coils each including a transmitter coil and a pair of receiver coils and located between two spiraled pole magnets which are arranged to produce an oblique magnetic field about the exterior of a tool body carrying the two spiraled pole magnets and the sets of sensor coils, each set of sensor coils being spaced about 180° apart from the other set of sensor coils and being arranged at an angle relative to the oblique magnetic field.

* * * * *